US009449425B2

(12) United States Patent
Kim et al.

(10) Patent No.: US 9,449,425 B2
(45) Date of Patent: Sep. 20, 2016

(54) APPARATUS AND METHOD FOR GENERATING MEDICAL IMAGE

(71) Applicant: SAMSUNG ELECTRONICS CO., LTD., Suwon-si (KR)

(72) Inventors: Yun Tae Kim, Hwaseong-si (KR); Ji Young Hong, Seongnam-si (KR); Jung Ho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 345 days.

(21) Appl. No.: 14/156,623

(22) Filed: Jan. 16, 2014

(65) Prior Publication Data
US 2014/0198102 A1 Jul. 17, 2014

(30) Foreign Application Priority Data

Jan. 16, 2013 (KR) .................. 10-2013-0004682

(51) Int. Cl.
| | |
|---|---|
| G06T 15/08 | (2011.01) |
| G06T 19/20 | (2011.01) |
| A61B 8/00 | (2006.01) |
| A61B 8/08 | (2006.01) |

(52) U.S. Cl.
CPC ............ *G06T 15/08* (2013.01); *A61B 8/466* (2013.01); *A61B 8/483* (2013.01); *G06T 19/20* (2013.01); *A61B 8/4405* (2013.01); *A61B 8/56* (2013.01); *G06T 2210/41* (2013.01); *G06T 2219/2012* (2013.01)

(58) Field of Classification Search
None
See application file for complete search history.

(56) References Cited

U.S. PATENT DOCUMENTS

| | | | | |
|---|---|---|---|---|
| 5,254,978 A | * | 10/1993 | Beretta | G01J 3/52 345/601 |
| 6,906,727 B2 | * | 6/2005 | Weibrecht | G06T 11/001 345/581 |
| 7,177,465 B1 | * | 2/2007 | Takahira | H04N 1/6058 358/1.9 |

(Continued)

FOREIGN PATENT DOCUMENTS

| | | |
|---|---|---|
| JP | 2012-005593 A | 1/2012 |
| JP | 2012-055687 A | 3/2012 |

(Continued)

OTHER PUBLICATIONS

Silverstein et al.; Automatic perceptual color map generation for realistic volume visualization; Journal of Biomedical Informatics; vol. 41 Issue 6, pp. 927-935; Dec. 2008.*

(Continued)

*Primary Examiner* — Carlos Perromat
(74) *Attorney, Agent, or Firm* — Sughrue Mion, PLLC

(57) ABSTRACT

Disclosed herein are a medical image generation apparatus and medical image generation method that realistically display an object or inner tissues of the object. The medical image generation apparatus includes a sample image extractor configured to extract a sample image from an original image containing color information of an object, a color gamut modeler configured to model a color gamut of the sample image to have a predetermined shape, a 2D color map generator configured to generate a 2D color map based on the modeled color gamut, a volume data generator configured to generate 3D volume data based on a sectional image of inner tissues of the object, and a control unit configured to generate a 3D color medical image by applying values of the 2D color map to a 3D grayscale medical image acquired by volume rendering of the 3D volume data.

20 Claims, 24 Drawing Sheets

(56) References Cited

U.S. PATENT DOCUMENTS

| | | | | |
|---|---|---|---|---|
| 8,724,894 B1 * | 5/2014 | Jensen | ............... | G06T 11/001 358/529 |
| 2005/0185837 A1 * | 8/2005 | Takano | ............... | H04N 1/4072 382/162 |
| 2009/0096807 A1 * | 4/2009 | Silverstein | ............ | G06T 11/001 345/593 |
| 2009/0184955 A1 | 7/2009 | Thiele | | |
| 2010/0039443 A1 * | 2/2010 | Mizukura | ............ | H04N 1/6058 345/590 |
| 2011/0187735 A1 * | 8/2011 | Kondoh | ............... | G09G 3/2003 345/589 |
| 2011/0270086 A1 * | 11/2011 | Hoctor | ............... | A61B 8/4488 600/443 |
| 2012/0127174 A1 * | 5/2012 | Naidu | ............... | G06T 11/001 345/419 |
| 2013/0063425 A1 * | 3/2013 | Watanabe | ............... | G06T 19/00 345/419 |

FOREIGN PATENT DOCUMENTS

| KR | 10-2009-0014112 A | 2/2009 |
|---|---|---|
| KR | 10-2010-0040557 A | 4/2010 |

OTHER PUBLICATIONS

Welsh et al.; Transferring color to greyscale images; ACM Transactions on Graphics (TOG)—Proceedings of ACM SIGGRAPH 2002; vol. 21 Issue 3, pp. 277-283; Jul. 2002.*

* cited by examiner

APPARATUS AND METHOD FOR GENERATING MEDICAL IMAGE

CROSS-REFERENCE TO RELATED APPLICATION(S)

This application claims the benefit of Korean Patent Application No. 10-2013-0004682, filed on Jan. 16, 2013 in the Korean Intellectual Property Office, the disclosure of which is incorporated herein by reference in its entirety.

BACKGROUND

1. Field

Exemplary embodiments of the present disclosure relate to an apparatus and method for generating a medical image to realistically display an object or inner tissues of the object.

2. Description of the Related Art

Research into medical imaging apparatuses is actively being conducted to go along with an increasing interest in improving the health of people. Examples of medical imaging apparatuses may include an X-ray imaging apparatus, an X-ray fluoroscopy apparatus, a computerized tomography (CT) scanner, a magnetic resonance imaging (MRI) apparatus, a positron emission tomography (PET) apparatus, and an ultrasonic diagnostic apparatus.

These medical imaging apparatuses display a 2D or 3D medical image of an object. A 2D medical image refers to a sectional image of inner tissues of an object. A 3D medical image refers to an image acquired through volume rendering of 3D volume data generated based on a plurality of sectional images.

The 2D and 3D medical images may be grayscale images or color images. Grayscale images are limited in the ability to provide a realistic image of an object, and thus, color images are currently the norm. Such color images may be acquired by mapping a grayscale image with colors that are similar to those of inner tissues of an object.

However, colors used in mapping are arbitrarily selected and thus, there remain limitations in providing a more realistic color image.

SUMMARY

Therefore, it is an aspect of the present disclosure to provide an apparatus and method for generating a medical image to realistically display an object or inner tissues of the object.

Additional aspects of the exemplary embodiments will be set forth in part in the description which follows and, in part, will be obvious from the description, or may be learned by practice of the exemplary embodiments.

In accordance with an aspect of an exemplary embodiment, an apparatus configured to generate a medical image includes a sample image extractor configured to extract a sample image from an original image containing color information of an object, a color gamut modeler configured to model a color gamut of the sample image to have a predetermined shape, a 2D color map generator configured to generate a 2D color map based on the modeled color gamut, a volume data generator configured to generate 3D volume data based on at least one sectional image of inner tissues of the object, and a control unit configured to generate a 3D color medical image by applying values of the 2D color map to a 3D grayscale medical image acquired by volume rendering of the 3D volume data.

In accordance with another aspect of an exemplary embodiment, a method of generating a medical image includes extracting a sample image from an original image containing color information of an object, modeling a color gamut of the sample image to have a predetermined shape, generating a 2D color map based on the modeled color gamut, generating 3D volume data based on a sectional image of inner tissues of the object, and generating a 3D color medical image by applying values of the 2D color map to a 3D grayscale medical image acquired through volume rendering of the 3D volume data.

BRIEF DESCRIPTION OF THE DRAWINGS

The patent or application file contains at least one drawing executed in color. Copies of this patent or patent application with color drawing(s) will be provided by the Office upon request and payment of the necessary fee.

These and/or other aspects of the exemplary embodiments will become apparent and more readily appreciated from the following description of the exemplary embodiments, taken in conjunction with the accompanying drawings of which.

DETAILED DESCRIPTION

Figure 1:
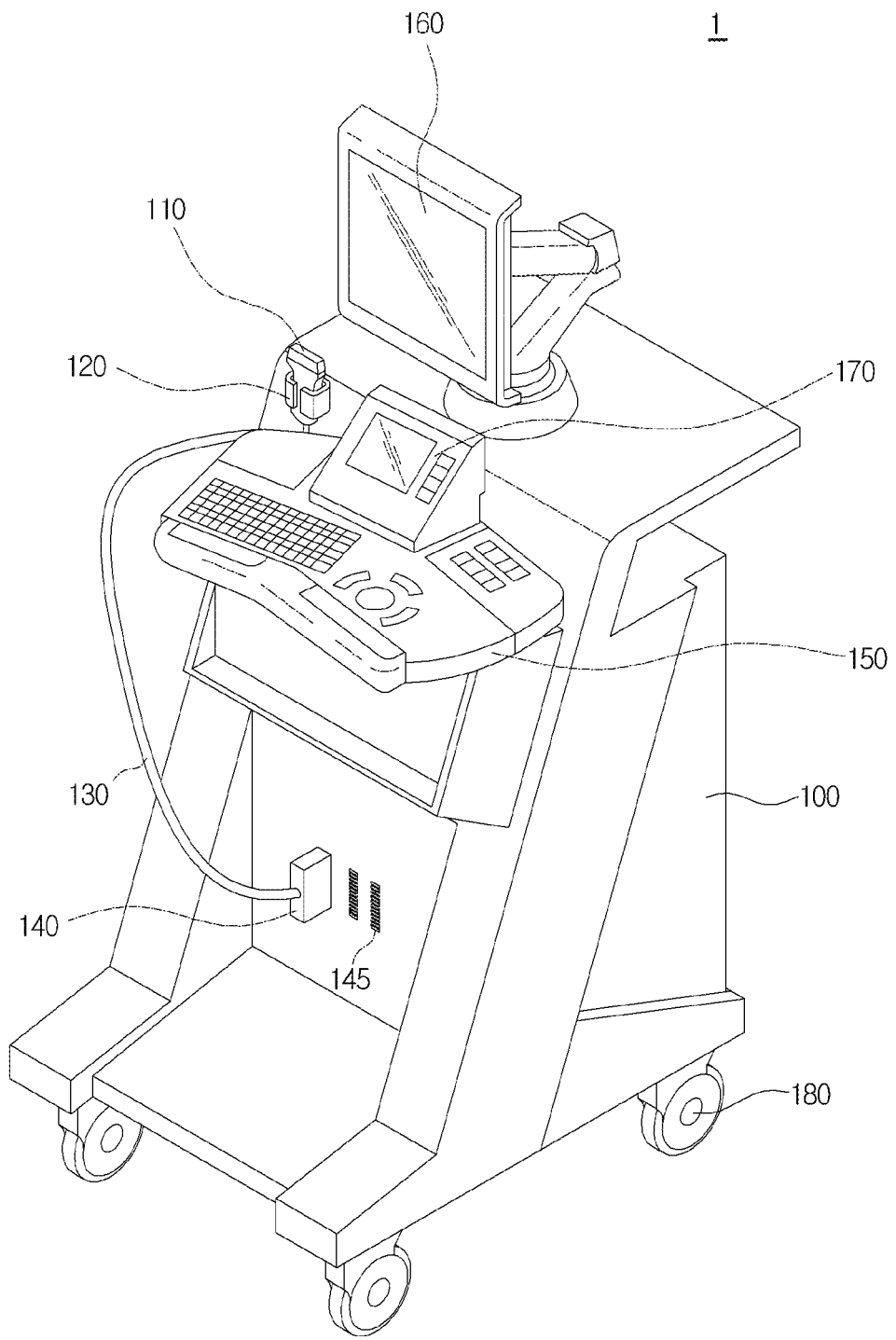
FIG. 1 is a perspective view of an ultrasonic diagnostic apparatus according to an exemplary embodiment.

The advantages and features of the exemplary embodiments and the way of attaining such advantages and features will become apparent with reference to exemplary embodiments described below in detail in conjunction with the accompanying drawings. Exemplary embodiments, however, may be embodied in many different forms and should not be constructed as being limited to exemplary embodiments set forth herein. Rather, these exemplary embodiments are provided so that this disclosure will be thorough and complete and will fully convey the scope to those skilled in the art. The scope of the exemplary embodiments should be defined by the claims.

Hereinafter, a medical image generation apparatus and medical image generation method according to exemplary embodiments will be described in detail with reference to the accompanying drawings. In the drawings, like reference numerals denote like elements.

A medical image generation apparatus according to an exemplary embodiment may refer to one of an X-ray imaging apparatus, an X-ray fluoroscopy apparatus, a computerized tomography (CT) scanner, a magnetic resonance imaging (MRI) apparatus, a positron emission tomography (PET) apparatus, and an ultrasonic diagnostic apparatus. However, exemplary embodiments are not limited to the above examples, and may include various other types of medical apparatuses so long as the medical apparatuses generate three-dimensional volume data from a plurality of section images of an inner tissue of an object. In the following description, for convenience of explanation, an ultrasonic diagnostic apparatus will be described as a medical image generation apparatus by way of example.

Ultrasonic diagnostic apparatuses irradiate an ultrasound signal towards a target site inside a human body through the surface of the human body and obtain a sectional image of a soft tissue or a blood flow image in a non-invasive manner using information of an ultrasound signal (i.e., ultrasound echo signal) reflected from the target site.

Ultrasonic diagnostic apparatuses are smaller in size and cheaper than other image diagnostic apparatuses, such as X-ray imaging apparatuses, CT scanners, MRI apparatuses, nuclear medicine diagnostic apparatuses, and the like. In addition, ultrasonic diagnostic apparatuses enable real-time display of a diagnosis image and are safe because there is no risk of exposure to X-rays. Thus, such ultrasonic diagnostic apparatuses are widely used in diagnosis of the heart, breast and abdomen, urological diagnosis, and diagnosis in obstetrics and gynecology.

FIG. 1 is a perspective view of an ultrasonic diagnostic apparatus 1 according to an exemplary embodiment. As illustrated in FIG. 1, the ultrasonic diagnostic apparatus 1 includes a main body 100, a probe 110, an input unit 150, a main display unit 160, and a sub display unit 170.

Figure 2:
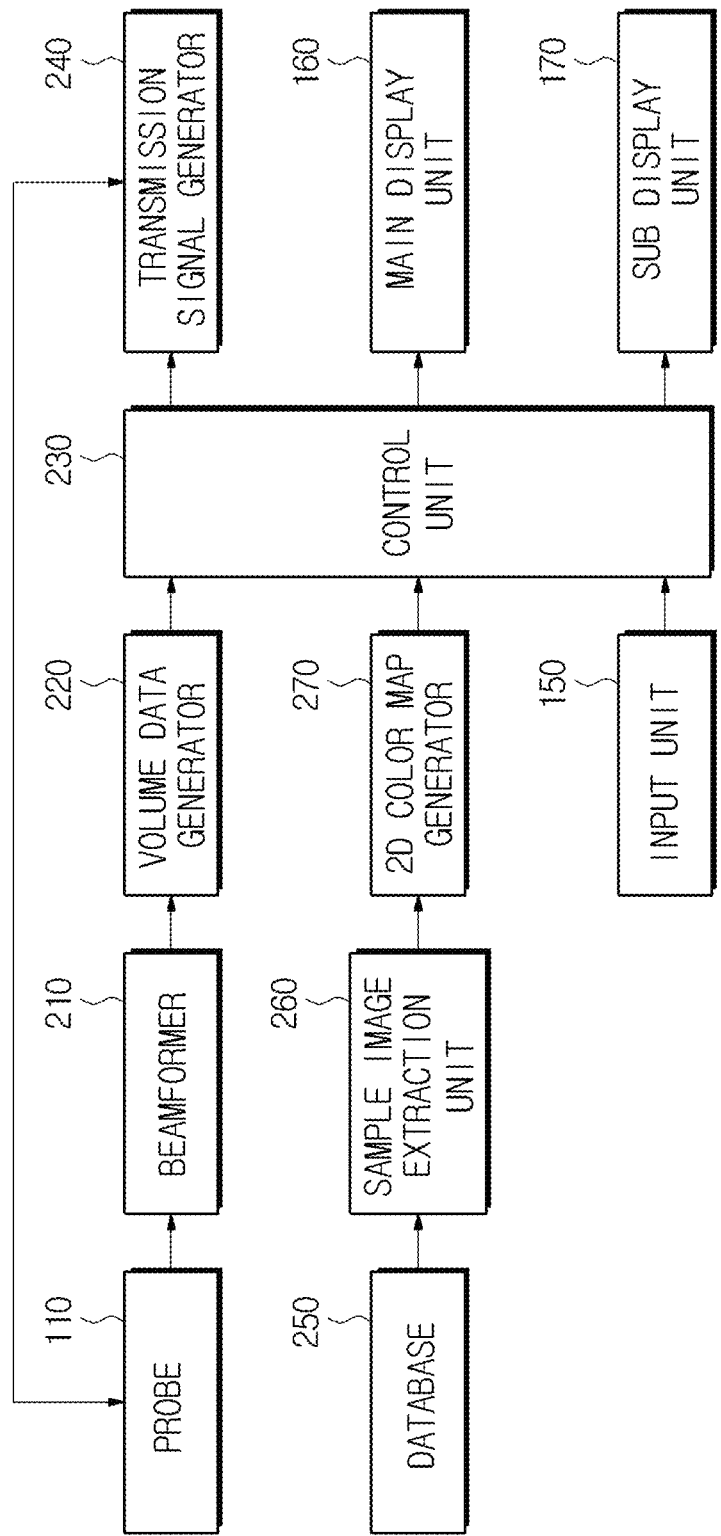
FIG. 2 is a block diagram illustrating the control configuration of the ultrasonic diagnostic apparatus according to an exemplary embodiment.

The main body 100 accommodates main constituent elements of the ultrasonic diagnostic apparatus 1, e.g., a transmission signal generator 240 (see FIG. 2). When an operator inputs an ultrasonic diagnosis command, the transmission signal generator 240 may generate a transmission signal and transmit the transmission signal to the probe 110.

The main body 100 is provided at one side thereof with at least one female connector 145. A male connector 140 connected to a cable 130 may be physically coupled to the female connector 145. The transmission signal generated by the transmission signal generator 240 may be transmitted to the probe 110 via the male connector 140 connected to the female connector 145 of the main body 100 and the cable 130.

The main body 100 is provided at a bottom side thereof with a plurality of casters 180 to provide mobility of the ultrasonic diagnostic apparatus 1. The casters 180 are configured to fix the ultrasonic diagnostic apparatus 1 at a particular place or move the ultrasonic diagnostic apparatus 1 in a particular direction.

The probe 110 may contact the body surface of an object (e.g., the abdomen of a pregnant woman) and transmit and receive ultrasound signals. In particular, the probe 110 transmits the transmission signal received by the main body 100, e.g., an ultrasound signal, into an object, e.g., a human body, receives an ultrasound echo signal reflected from a particular site (e.g., a fetus) inside the human body, and transmits the ultrasound echo signal to the main body 100.

To implement this operation, the probe 110 may be provided at one end thereof with a plurality of ultrasound transducers to generate ultrasonic waves according to an electrical signal.

The ultrasound transducers may generate ultrasonic waves upon receiving AC power. In particular, the ultrasound transducers may receive AC power from an external power supply device or an internal charge device, for example, a battery. The ultrasonic waves may be generated as piezoelectric oscillators or thin films of the ultrasound transducers may oscillate upon receiving AC power.

The ultrasound transducers, may be implemented as various kinds of ultrasound transducers, such as, for example, a magnetostrictive ultrasound transducer using the magnetostrictive effect of a magnetic substance, a piezoelectric ultrasound transducer using the piezoelectric effect of a piezoelectric material, and a capacitive micro-machined ultrasound transducer that transmits and receives ultrasonic waves using vibration of hundreds or thousands of micromachined thin films.

The ultrasound transducers may be arranged as a linear array or a convex array. A cover to cover the ultrasound transducers may be provided over the ultrasound transducers.

The probe 110 is provided at the other end thereof with a cable 130 connected thereto and the male connector 140 is connected to an end of the cable 130. The male connector 140 is physically coupled to the female connector 145 of the main body 100.

The input unit 150 receives an instruction related to an operation of the ultrasonic diagnostic apparatus 1. For example, the input unit 150 may receive an instruction to select a mode, such as an amplitude mode (A-mode), a brightness mode (a B-mode), and a motion mode (an M-mode), an ultrasonic diagnosis initiation instruction, and the like. The instruction received by the input unit 150 may be transmitted to the main body 100 through wired or wireless communication technologies.

The input unit 150 may include, for example, at least one of a touchpad, a keyboard, a foot switch, and a foot pedal. The touchpad or keyboard may be implemented as a hardware element located at an upper portion of the main body 100. The keyboard may include at least one of a switch, a key, a wheel, a joystick, a trackball, and a knob. As another example, the keyboard may be implemented as a software element, such as a graphical user interface. In this case, the keyboard may be displayed via the sub display unit 170 or the main display unit 160. The foot switch or the foot pedal may be provided at a lower position of the main body 100, and the operator may control an operation of the ultrasonic diagnostic apparatus 1 using the foot pedal.

A probe holder 120 to hold the probe 110 is provided near the input unit 150. A user of the ultrasonic diagnostic apparatus 1 (e.g., a medical professional) may place the probe 110 in the probe holder 120 to store the probe 110 therein when the ultrasonic diagnostic apparatus 1 is not in use. FIG. 1 illustrates a case in which a single probe holder 120 is provided near the input unit 150, but exemplary embodiments are not limited thereto. The position or number of the probe holders 120 may be variously changed according to an overall design of the ultrasonic diagnostic apparatus 1 or design or position of some elements thereof.

The sub display unit 170 may be provided at the main body 100. FIG. 1 illustrates a case in which the sub display unit 170 is located above the input unit 150. The sub display unit 170 may display applications related to an operation of the ultrasound image generating apparatus. The sub display unit 170 may be realized as, for example, a cathode ray tube (CRT), a liquid crystal display (LCD), or the like. The sub display unit 170 may display menus or instructions needed for ultrasonic diagnosis.

The main display unit 160 is provided on the main body 100. FIG. 1 illustrates a case in which the main display unit 160 is located above the sub display unit 170, although it is understood that the main display unit 160 may be located in other places as well. The main display unit 160 may be realized as, for example, a CRT or a LCD device. The main display unit 160 may display an ultrasound image acquired through an ultrasonic diagnosis process. The ultrasound image displayed on the main display unit 160 may include at least one of a two-dimensional (2D) grayscale ultrasound image, a 2D color ultrasound image, a three-dimensional (3D) grayscale ultrasound image, and a 3D color ultrasound image.

Although FIG. 1 illustrates that the ultrasonic diagnostic apparatus 1 includes both the main display unit 160 and the sub display unit 170, the sub display unit 170 may be omitted from some exemplary embodiments. In this case, applications, menus, or the like which are displayed on the sub display unit 170 according to an exemplary embodiment may instead be displayed on the main display unit 160.

In addition, at least one of the main display unit 160 and the sub display unit 170 may be installed to be separable from the main body 100.

The ultrasonic diagnostic apparatus 1 according to the exemplary embodiment has been described above with reference to FIG. 1. Hereinafter, a control configuration of the ultrasonic diagnostic apparatus 1 and functions of elements thereof will be described in more detail with reference to FIGS. 2 through 19.

FIG. 2 is a block diagram illustrating the control configuration of the ultrasonic diagnostic apparatus 1 according to an exemplary embodiment.

As illustrated in FIG. 2, the ultrasonic diagnostic apparatus 1 includes the transmission signal generator 240, the probe 110, a beamformer 210, a volume data generator 220, a database 250, a sample image extraction unit 260 (e.g., sample image extractor), a 2D color map generator 270, a control unit 230, the input unit 150, a storage unit (not shown), the main display unit 160, and the sub display unit 170.

Among these elements, the probe 110, the input unit 150, the main display unit 160, and the sub display unit 170 have already been described above with reference to FIG. 1, and thus, a detailed description thereof is omitted.

Figure 3:
FIG. 3 illustrates a plurality of baby images.

The database 250 stores a plurality of original images containing color information of an object. For example, if the object is an internal organ of a human body, the original images may be captured organ images. If the object is blood vessels inside the human body, the original images may be captured images of the blood vessels. If the object is a fetus, the original images may be captured images of a face of the fetus. In this regard, the images of the face of the fetus may include only the face or the face and the surrounding environment. FIG. 3 shows 12 baby images including faces and surrounding environments.

The original images may be acquired by an imaging device included in the ultrasonic diagnostic apparatus 1 or by a separate imaging device. The original images may be divided according to type and stored in the database 250. For example, the original images may be sorted into organ images, blood vessel images, and baby images. In particular, the baby images may be divided according to race and stored in the database 250. For example, the baby images may be divided into images of the black, Asian and white races and stored in the database 250. Selection of the object and/or race may be performed via the input unit 150 before starting ultrasonic diagnosis or during ultrasonic diagnosis.

In the following description, a case in which the original images are baby images will be described.

The sample image extraction unit 260 extracts at least one sample image from a plurality of baby images stored in the database 250. In particular, the sample image extraction unit 260 may extract m sample images having a size of n×n from one baby image. According to an exemplary embodiment, m may be a fixed value. According to another exemplary embodiment, m may be adjusted by an operator of the ultrasonic diagnostic apparatus 1.

The sample image is extracted from a baby face region. Thus, when a baby image includes the face and the surrounding environment, the sample image extraction unit 260 detects a face region from the baby image, followed by extraction of m sample images from the detected face region. When the baby image includes only the face, the process of detecting the face region is not performed.

Information as to whether the baby image includes both the face and the surrounding environment or only the face may be included in metadata of the baby image. That is, the sample image extraction unit 260 checks the metadata of the baby image to determine whether the corresponding baby image includes both the face and the surrounding environment or only the face. When the baby image includes the face and the surrounding environment, a baby face region is detected from the baby image.

Figure 4:
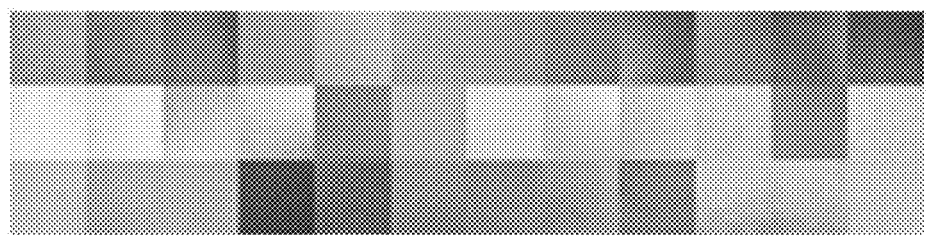
FIG. 4 illustrates sample images extracted from the baby images illustrated in FIG. 3.

FIG. 4 illustrates sample images extracted from the 12 baby images illustrated in FIG. 3. Referring to FIG. 4, three sample images have been extracted from each of the 12 baby images, and thus, the number of the sample images according to this example is 36.

The 2D color map generator 270 generates a 2D color map based on a plurality of sample images. To generate the 2D color map, the 2D color map generator 270 refers to a lookup table in which colors used for mapping of a 3D grayscale ultrasound image are listed using 2D coordinates. To generate the 2D color map, the 2D color map generator 270 may perform color space conversion of the sample image, color gamut modeling of the sample image, and mapping based on the modeled color gamut.

Figure 5:
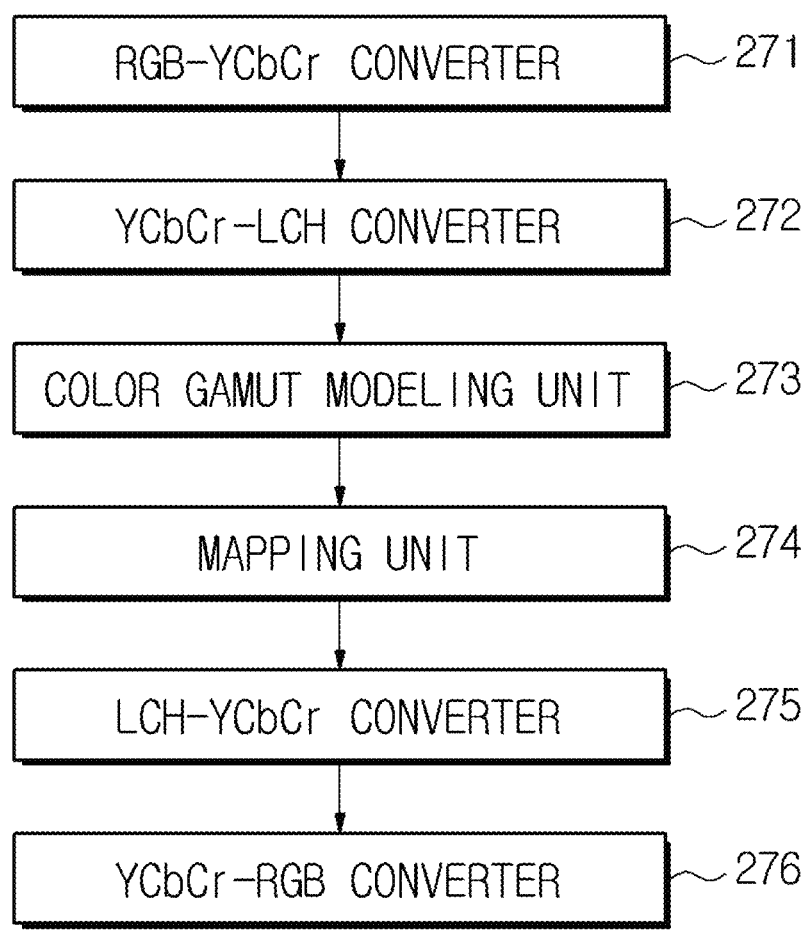
FIG. 5 is a block diagram specifically illustrating the control configuration of a 2D color map generator of the ultrasonic diagnostic apparatus of FIG. 2.

FIG. 5 is a block diagram specifically illustrating a configuration of the 2D color map generator 270. As illustrated in FIG. 5, the 2D color map generator 270 may include an RGB-YCbCr converter 271, a YCbCr-LCH converter 272, a color gamut modeling unit 273 (e.g., color gamut modeler), a mapping unit 274, an LCH-YCbCr converter 275, and a YCbCr-RGB converter 276.

A plurality of sample images extracted by the sample image extraction unit 260 may be color images represented in RGB color space. This indicates that each of a plurality of pixels of the sample images is composed of R, G and B values. To generate a 2D color map based on the samples images, each pixel of which is composed of R, G and B values, the color space of the sample images may be converted. The RGB-YCbCr converter 271 and the YCbCr-LCH converter 272 may perform color space conversion.

The RGB-YCbCr converter 271 converts the color space of the sample images into the YCbCr color space from the RGB color space. The YCbCr color space is used in imaging systems and composed of Y, Cb and Cr values. In this regard, Y denotes a luma component, Cb denotes a blue-difference chroma component, and Cr denotes a red-difference chroma component. Conversion from the RGB color space into the YCbCr color space is performed using Equation 1 below:

$Y=0.299 \times R+0.587G+0.114B$ $Cb=-0.1687 \times R-0.3313G+0.5B$ $Cr=0.5R-0.4187G-0.0813B$ [Equation 1]

Figure 6:
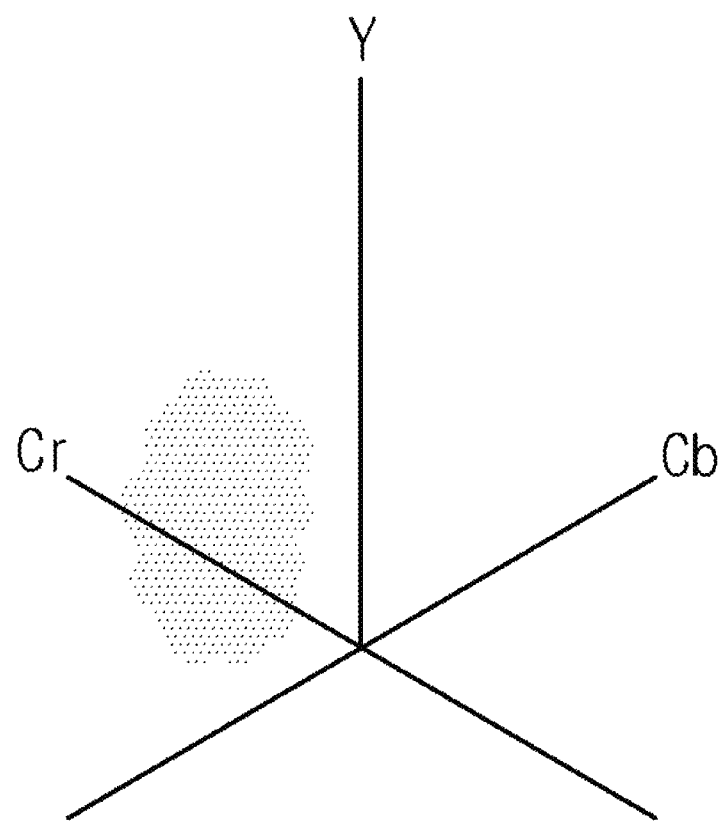
FIG. 6 is a view illustrating an YCbCr color space in which a value of each of a plurality of pixels of sample images is represented.

Once conversion into the YCbCr color space is completed, each pixel of the sample images has Y, Cb and Cr values. The Y, Cb and Cr values of each pixel of the sample images may be represented in the YCbCr color space, as illustrated in FIG. 6.

Referring back to FIG. 5, the YCbCr-LCH converter 272 converts the color space of the sample images into the LCH color space from the YCbCr color space.

Conversion from the YCbCr color space into the LCH color space is performed using Equation 2 below. Once conversion into the LCH color space is completed, each pixel of the sample images has L (lightness), C (chroma) and H (hue angle) values:

$$L = Y$$
$$C = \sqrt{Cb^2 + Cr^2}$$
$$H = a\tan\left(\frac{Cr}{Cb}\right)$$
[Equation 2]

Referring back to FIG. 5, the color gamut modeling unit 273 performs color gamut modeling based on color space conversion results obtained by the RGB-YCbCr converter 271 and color space conversion results obtained by the YCbCr-LCH converter 272. According to an exemplary embodiment, color gamut modeling refers to defining a boundary of a color gamut of the sample images so that the color gamut of the sample images has a predetermined shape. For example, the color gamut modeling unit 273 may model the color gamut of the sample images to have a circular, oval, or polygonal shape. Hereinafter, a case of modeling a color gamut of the sample images to have a polygonal shape will be described by way of example.

As modeling of the color gamut of the sample images into a polygonal shape with various angles is performed, a more realistic 3D color ultrasound image may be generated. When modeling is performed to have a polygonal shape with various angles, however, a computational load for color gamut modeling correspondingly increases. Thus, the modeling of the color gamut of the sample images into the polygonal shape may be determined taking into consideration at least one of a desired quality of the 3D color ultrasound image and processing abilities of the ultrasonic diagnostic apparatus 1.

Information on such color gamut modeling may be set when the ultrasonic diagnostic apparatus 1 is released. According to an exemplary embodiment, set values for the color gamut modeling may be fixed. According to another exemplary embodiment, set values for the color gamut modeling may be adjustable by an operator before starting an ultrasonic diagnosis or during ultrasonic diagnosis. Hereinafter, a process of modeling color gamut of the sample images into a hexagonal shape will be described by way of example.

Figure 7:
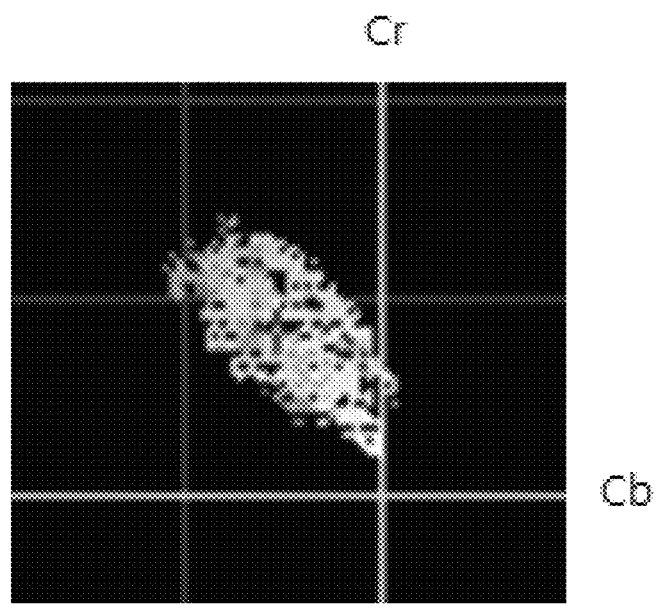
FIG. 7 is an image showing results of projecting values represented in the YCbCr color space of FIG. 6 onto a CbCr plane.

To perform color gamut modeling, the color gamut modeling unit 273 projects values represented in the YCbCr color space of FIG. 6 onto a CbCr plane. As a result, a Cb-Gr graph as illustrated in FIG. 7 may be obtained. As seen with reference to FIG. 7, the color of the face of a baby is located in a second quadrant among quadrants of the CbCr plane.

Subsequently, the color gamut modeling unit 273 models a color gamut of the sample images illustrated in FIG. 7 to have a hexagonal shape. That is, the color gamut modeling unit 273 defines the boundary of the color gamut of the sample images by a hexagon. For this operation, the color gamut modeling unit 273 divides a range of hue angles represented in the LCH color space by 6. Points with the highest chroma values corresponding to the six respective ranges of hue angles are determined as vertices of the hexagon. In particular, assuming that the hue angles are in the range of 0° to 60° when values of each pixel of the sample images are represented in the LCH color space, points with the highest chroma corresponding to hue angles obtained by dividing this range by 6, i.e., 10°, 20°, 30°, 40°, 50°, and 60°, are determined as vertices of the hexagon on the CbCr plane.

Figure 8:
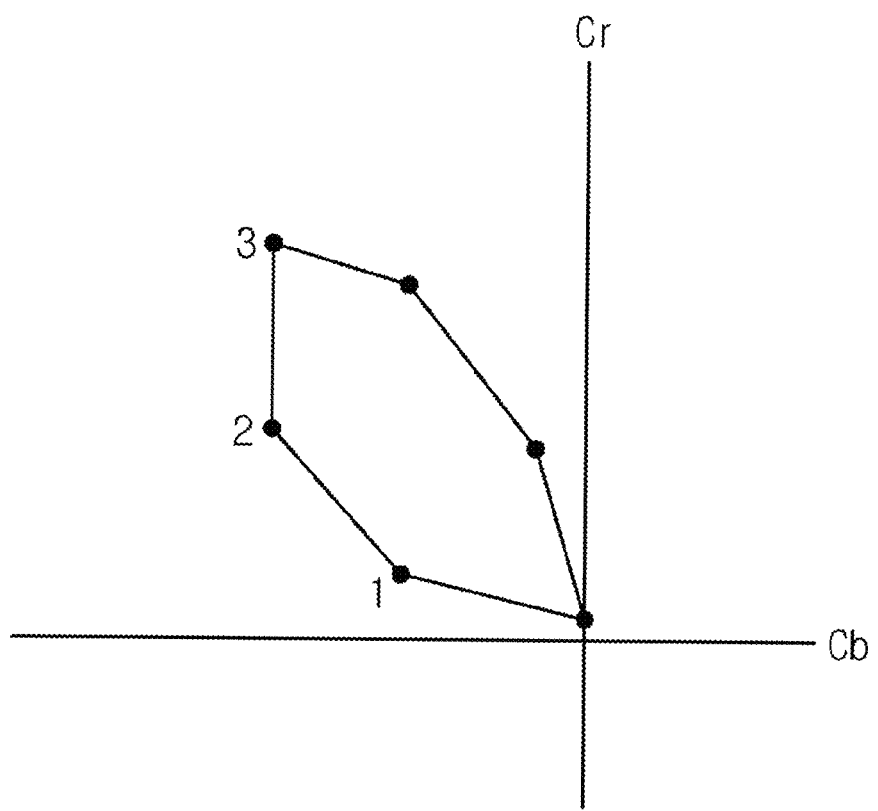
FIG. 8 is a view illustrating a polygonal color gamut model.

After determination of the vertices of the hexagon on the CbCr plane, the vertices are connected to one another. Thereafter, values of a hollow region inside the hexagon may be determined by interpolation. As a result, a modeled color gamut defined by a hexagon as illustrated in FIG. 8 may be obtained.

Figure 9:
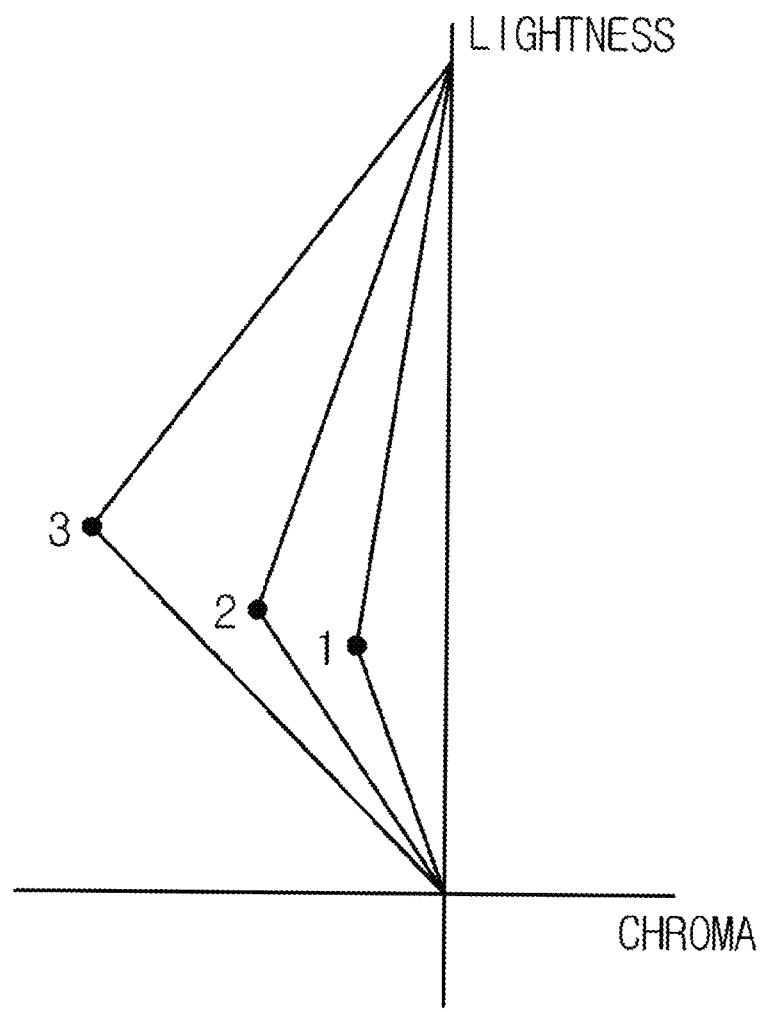
FIG. 9 is a view illustrating a relationship between lightness and chroma for each of a plurality of vertices of the polygonal shape obtained through color gamut modeling.

As described above, according to an exemplary embodiment, the color gamut modeling is implemented only on the CbCr plane without considering a lightness component. Thus, once color gamut modeling is completed, the color gamut modeling unit 273 calculates a lightness corresponding to the modeled color gamut. A relationship between lightness and chroma for each vertex of the hexagon obtained through color gamut modeling is illustrated in FIG. 9. In FIG. 9, vertices 1, 2 and 3 correspond to vertices 1, 2 and 3 of the hexagon defining the modeled color gamut. As illustrated in FIG. 9, when lightness has a median value, chroma has the highest value. In addition, when lightness has a higher or lower value than the median value, chroma decreases.

Figure 10:
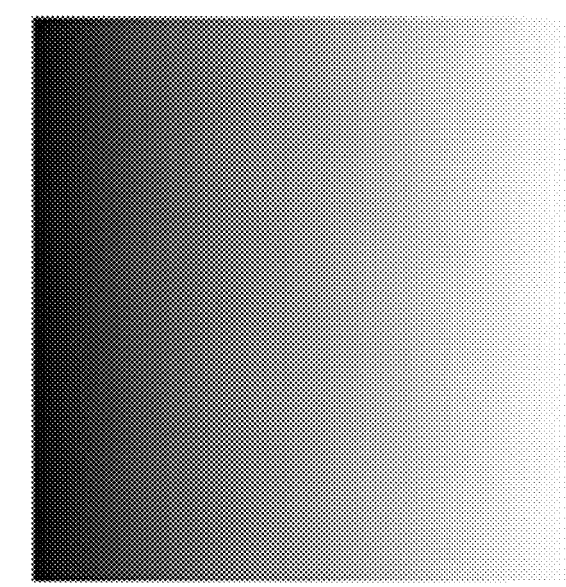
FIG. 10 is an image showing a 2D color map generated based on the modeled color gamut.

Referring back to FIG. 5, the mapping unit 274 (e.g., mapper) generates a 2D color map based on the modeled color gamut. That is, the mapping unit 274 maps lightness, chroma, and hue that correspond to the modeled color gamut to 2D coordinates, thereby generating a 2D color map. In particular, the mapping unit 274 performs a mapping process such that lightness and chroma vary along a horizontal axis of a 2D coordinate system and hue varies along a vertical axis of the 2D coordinate system. In this regard, a varying direction of lightness and chroma may correspond to a shading direction of a 3D grayscale ultrasound image. In addition, a varying direction of hue may correspond to a depth direction of the 3D grayscale ultrasound image. FIG. 10 is an image showing a 2D color map in which lightness and chroma increase along the horizontal axis and hue increases along the vertical axis.

To apply the 2D color map illustrated in FIG. 10 to a 3D grayscale ultrasound image, a value of each of a plurality of coordinates of the 2D color map should be converted into a value of a color space suitable for use in an imaging system. For example, lightness (L), chroma (C) and hue (H) values of each coordinate of the 2D color map should be converted into R, G and B values. Such color space conversion may be performed by the LCH-YCbCr converter 275 and the YCbCr-RGB converter 276.

Referring back to FIG. 5, the LCH-YCbCr converter 275 converts the L, C and H values of each coordinate of the 2D color map to Y, Cb and Cr values. By representing the generated Y, Cb and Cr values in a color space, a Cb-Cr graph, a Y-Cb graph, and a Y-Cr graph respectively illustrated in FIGS. 11 A through 11C may be obtained.

Figure 11A:
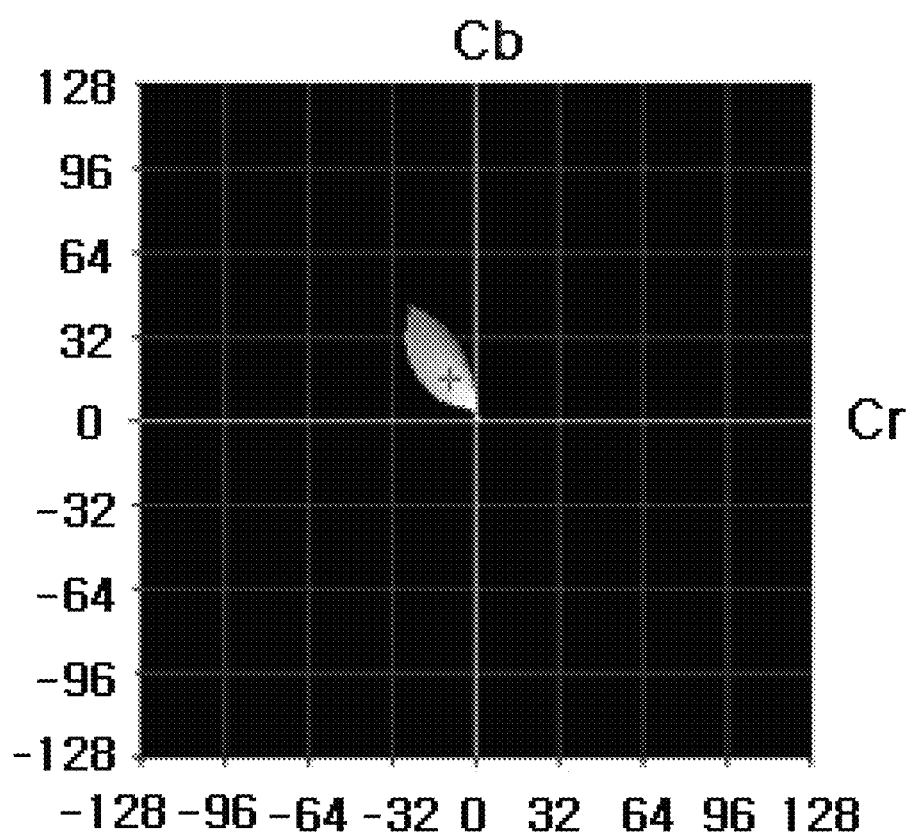
FIGS. 11A through 11C respectively illustrate a Cb-Cr graph, a Y-Cb graph, and a Y-Cr graph that represent YCbCr values of each of a plurality of coordinates of the 2D color map.

The Cb-Cr graph of FIG. 11A has a similar shape to that of the Cb-Cr graph illustrated in FIG. 7. In other words, a comparison of FIG. 7 and FIG. 11A confirms that the Cb-Cr graph obtained from the 2D color map has a similar shape to that of the Cb-Cr graph obtained from the sample image. Referring to the Y-Cb graph of FIG. 11B and the Y-Cr graph of FIG. 11C, chroma decreases when lightness increases or decreases based on a point with the highest chroma.

By representing Y, Cb and Cr values of each of a plurality of coordinates of a 1D color map in a color space, a Cb-Cr graph, a Y-Cb graph, and a Y-Cr graph respectively illustrated in FIGS. 12 A through 12C may be obtained.

Figure 11B:
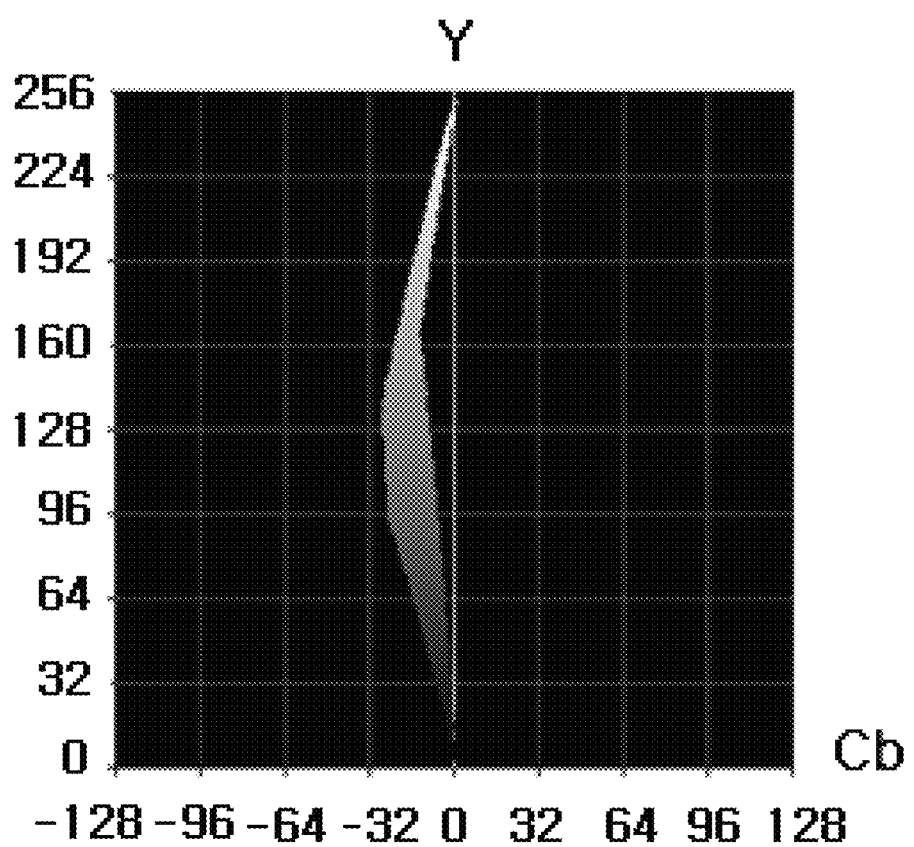
Figure 11C:
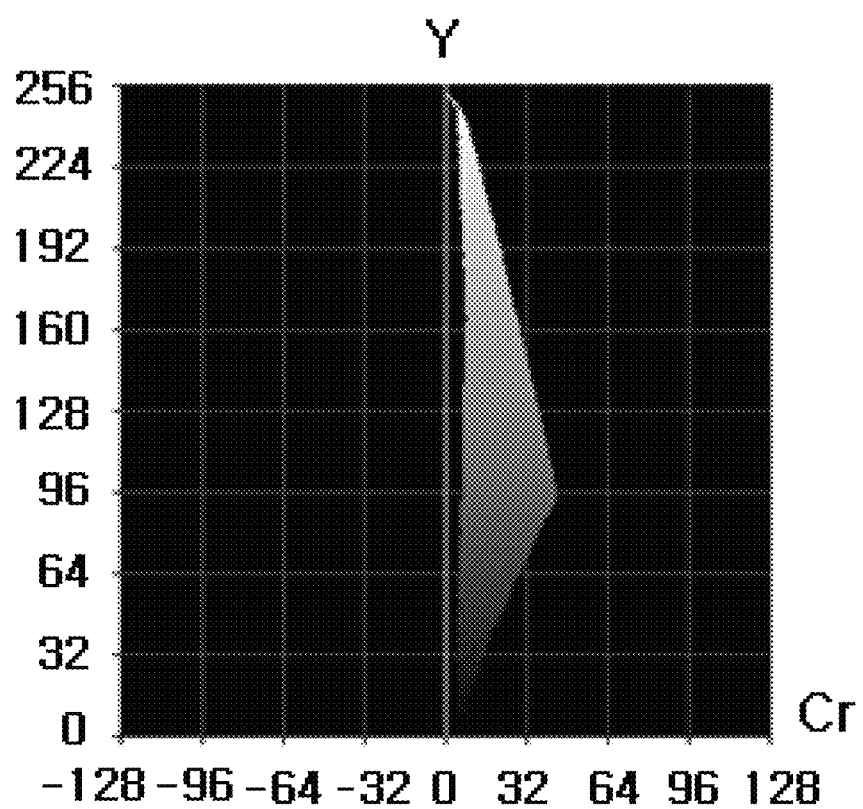
Figure 12A:
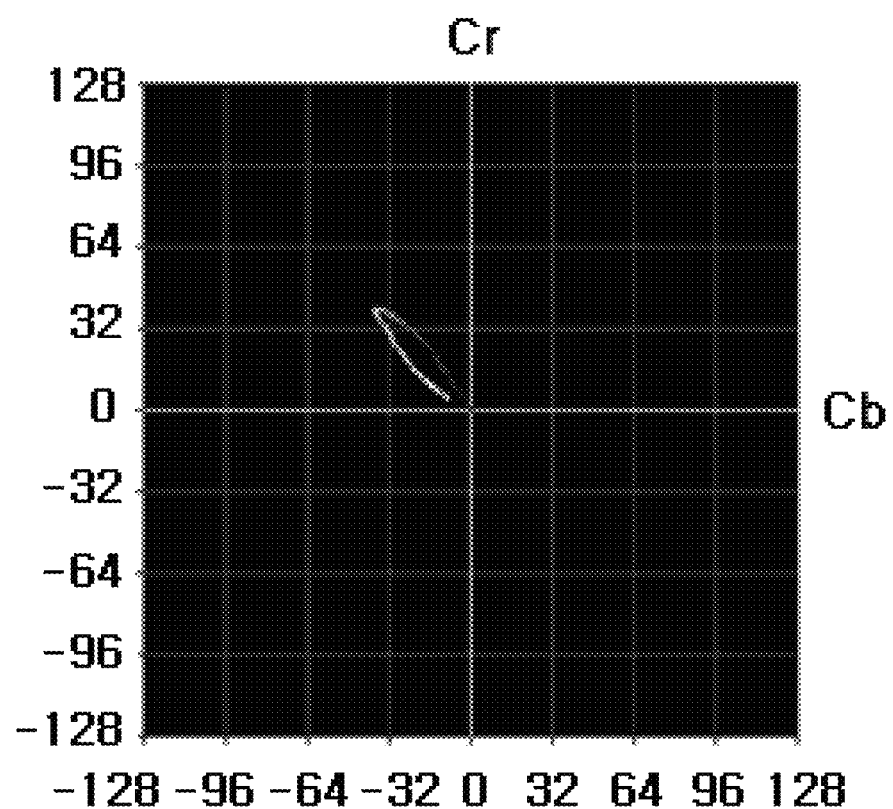
FIGS. 12A through 12C respectively illustrate a Cb-Cr graph, a Y-Cb graph, and a Y-Cr graph that represent YCbCr values of each of a plurality of coordinates of a conventional 1D color map.
Figure 12B:
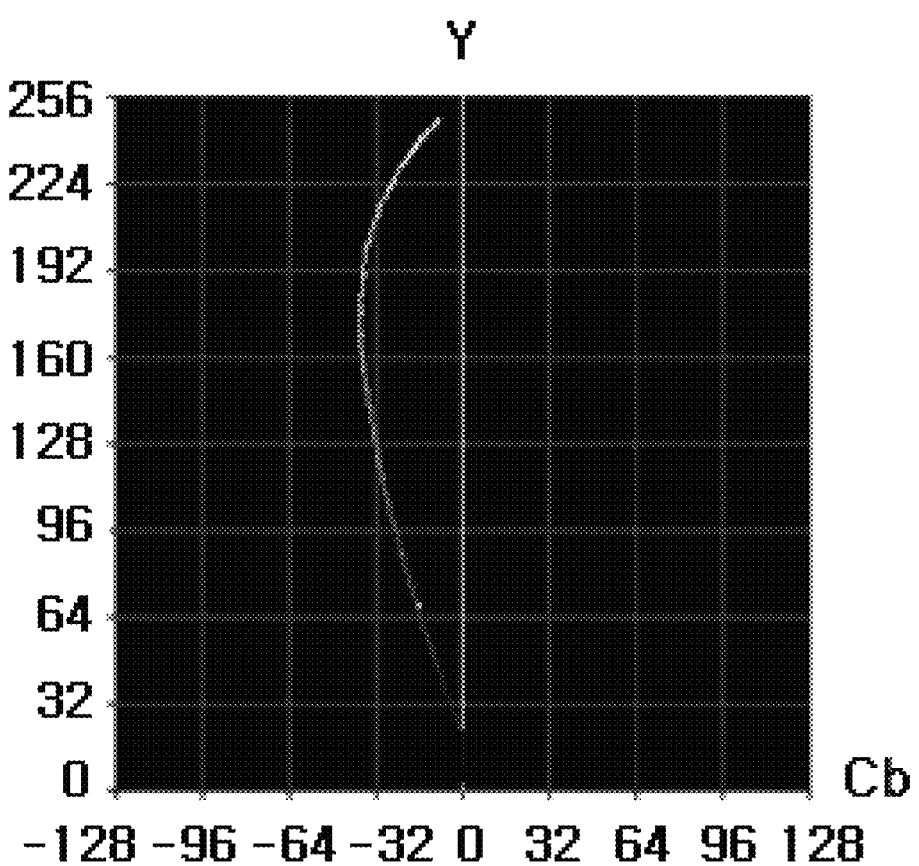
Figure 12C:
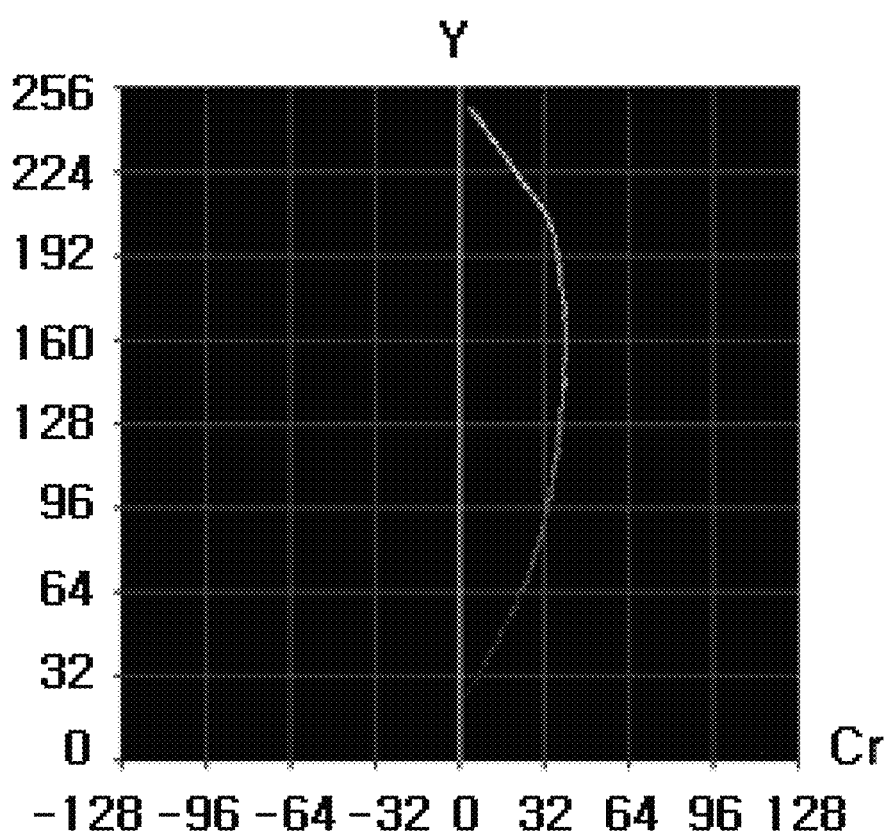

Through a comparison between the graphs of FIGS. 12A to 12C and the graphs of FIGS. 11A to 11C, it can be confirmed that the 2D color map according to the above-described exemplary embodiment has a wider color gamut than that of a conventional 1D color map. Thus, according to exemplary embodiments, when a 3D color ultrasound image is generated based on the 2D color map, it is possible to display colors more naturally as compared to a case in which a 3D color ultrasound image is generated based on the 1D color map.

Referring back to FIG. 5, the YCbCr-RGB converter 276 converts the Y, Cb and Cr values of each coordinate of the 2D color map into R, G and B values. As a result, each coordinate of the 2D color map is represented by R, G and B values.

Referring back to FIG. 2, the transmission signal generator 240 generates a transmission signal, taking into consideration positions and a focal point of the ultrasound transducers. According to an exemplary embodiment, the transmission signal refers to a high-voltage electrical signal to oscillate the ultrasound transducers. The generated transmission signal may be transmitted to the ultrasound transducers of the probe 110.

The ultrasound transducers of the probe 110 convert the transmission signal into an ultrasound signal, irradiate the ultrasound signal to an object, and receive an ultrasound echo signal from the object. The received ultrasound echo signal is transmitted to the beamformer 210.

Figure 13:
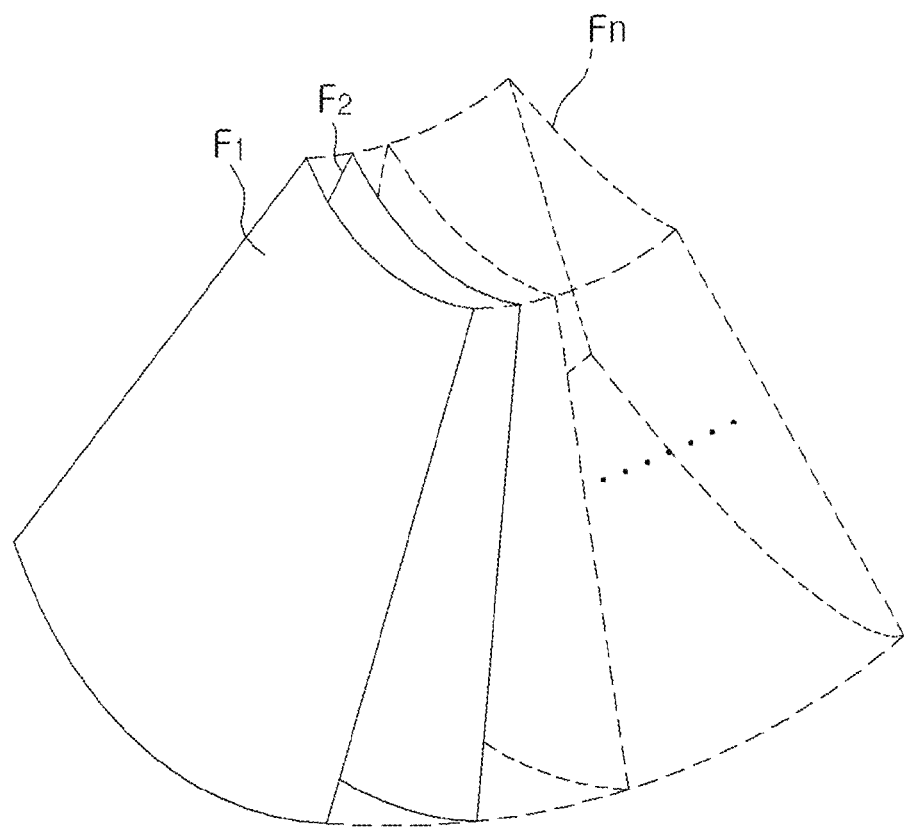
FIG. 13 is a view illustrating a plurality of sectional images.

The beamformer 210 converts the analog ultrasound echo signal into a digital signal. In addition, the beamformer 210 applies a time delay to the digital signal in consideration of the positions and focal point of the ultrasound transducers, and receives and focuses the digital signal to generate a focused signal. The focused signal generated by the beamformer 210 may be generated as sectional images of the object. A plurality of sectional images may be generated as illustrated in FIG. 13.

Figure 14:
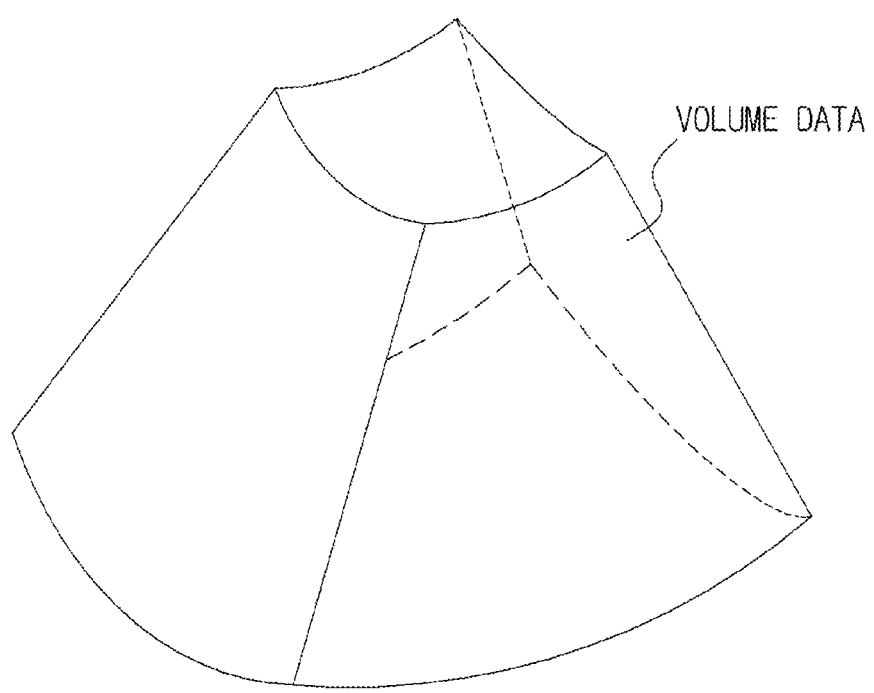
FIG. 14 is a view illustrating volume data based on the plurality of sectional images.

The volume data generator 220 generates 3D volume data for the object based on the plurality of sectional images generated by the beamformer 210, as shown in FIG. 14. According to an exemplary embodiment, the 3D volume data may be represented as a plurality of voxels. The term "voxel" as used herein is a combination of the terms "volume" and "pixel." While a pixel refers to a single point in a 2D plane, a voxel refers to a single point in 3D space. In addition, a pixel has X and Y coordinates, whereas a voxel has X, Y and Z coordinates.

Referring back to FIG. 2, the control unit 230 generates a 3D grayscale ultrasound image through volume rendering of the 3D volume data. The 3D grayscale ultrasound image may be understood as a 2D projection image of the 3D volume data.

The control unit 230 may perform volume rendering of the 3D volume data using one of many different types of the volume rendering methods known in the art. For example, the volume rendering methods may be classified into surface rendering and direct volume rendering methods.

Surface rendering is a method including extracting surface information from volume data based on a constant scalar value and spatial variation, and changing the extracted information into a geometrical element, such as a polygonal or curvilinear patch, to apply a conventional rendering method thereto. Examples of surface rendering techniques include a marching cubes algorithm and a dividing cubes algorithm.

Direct volume rendering is a method for direct rendering of volume data without an intermediate process of changing volume data into a geometrical element. Direct volume rendering directly provides visual information on the interior of an object and may be advantageous when displaying a semi-transparent structure. The direct volume rendering techniques may be classified into an object-order method and an image-order method according to the order in which volume data is accessed.

The object-order method is a method of determining pixel values by sequentially searching for 2D slices (e.g., an object), assuming that volume data consists of a stack of 2D slices.

The image-order method is a method of sequentially determining pixel values of an image according to a scan line order of the image. Ray-casting is an example of an image-order method. Ray-casting will be briefly described with reference to FIG. 15.

Figure 15:
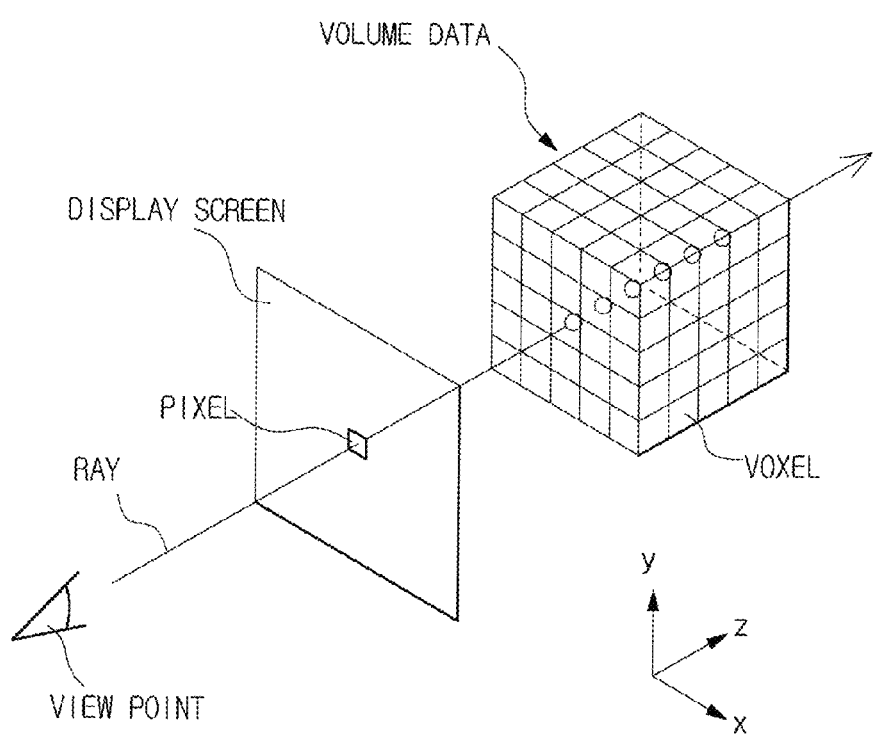
FIG. 15 is a view for explaining a concept of volume rendering.

An exemplary Ray-casting technique, according to an exemplary embodiment as illustrated in FIG. 15, includes emitting a virtual ray from an eye point to a predetermined pixel of a display screen, and detecting some voxels of volume data through which the ray passes. Then, a lightness value of the corresponding pixel is determined by accumulating lightness values of the detected voxels. According to another exemplary embodiment, the lightness value of the pixel may be determined as an average of the detected voxels or a weighted average of the detected voxels.

In addition to or instead of the above-described volume rendering methods, the control unit 230 may use ray-tracing. According to an exemplary embodiment, ray-tracing is a method to find light entering the observer's eyes by tracing ray paths one by one.

According to an exemplary embodiment, the control unit 230 may further perform shading, hidden surface removal, and the like during volume rendering. Such processes may be performed to compensate for data loss caused by 3D to 2D dimensional reduction and to display an image more naturally.

According to an exemplary embodiment, each of a plurality of pixels of the 3D grayscale ultrasound image generated as a result of the volume rendering process has a shading value and a depth value. The depth value of each pixel may be a depth value from a view point or a depth value from the origin in a 3D space in which volume data are represented.

Figure 16:
FIG. 16 illustrates a shadow image of a 3D grayscale ultrasound image generated by volume rendering.
Figure 17:
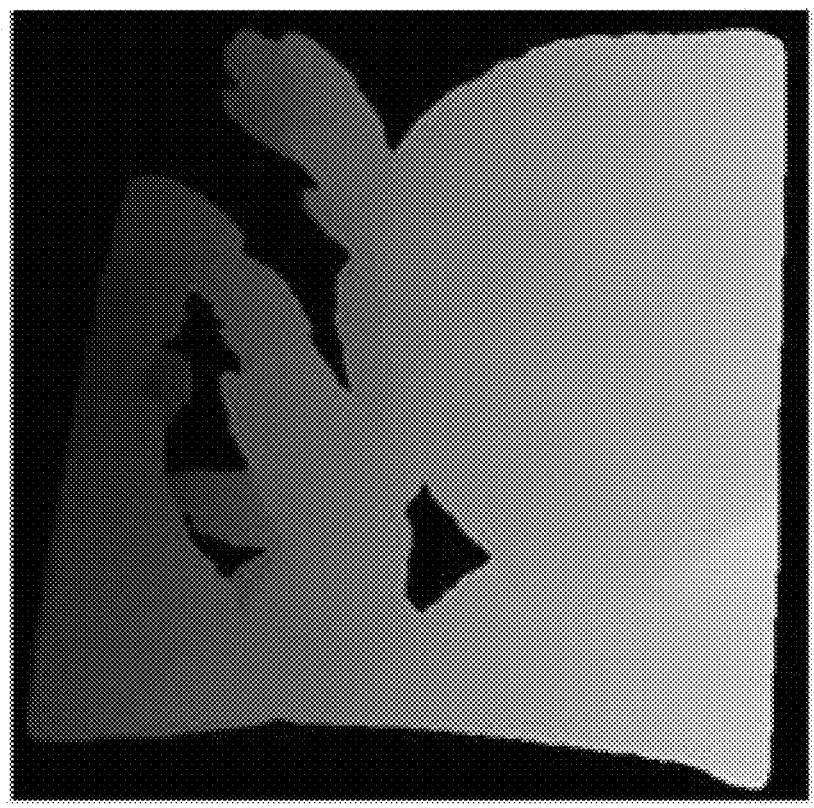
FIG. 17 illustrates a depth image of the 3D grayscale ultrasound image generated by volume rendering.

FIGS. 16 and 17 respectively illustrate a shadow image and a depth image of a 3D grayscale ultrasound image. The shadow image of FIG. 16 is an image displayed by separating only a shading value of each pixel of the 3D grayscale ultrasound image. In contrast, the depth image of FIG. 17 is as an image displayed by separating only a depth value of each pixel of the 3D grayscale ultrasound image.

Referring back to FIG. 2, the control unit 230 generates a 3D color ultrasound image by applying values of the 2D color map to each pixel of the 3D grayscale ultrasound image. In this regard, the values of the 2D color map to be applied to the pixels of the 3D grayscale ultrasound image may be determined based on the shading and depth values of each pixel of the 3D grayscale ultrasound image.

In particular, according to an exemplary embodiment, the control unit 230 searches for a coordinate corresponding to the shading and depth values of the pixel in the 2D color map. Thereafter, R, G and B values of the searched coordinate are applied to the corresponding pixel of the 3D grayscale ultrasound image. For example, it is assumed that a pixel on the first row and the first column of the 3D grayscale ultrasound image (hereinafter also referred to as "a first pixel") has a shading value of 10 and a depth value of 15. Given this condition, the control unit 230 applies R, G and B values of a coordinate represented in the 2D color map and having a horizontal axis value of 10 and a vertical axis value of 15 to the first pixel of the 3D grayscale ultrasound image. In such a manner, the control unit 230 applies values of the 2D color map to all of the pixels of the 3D grayscale ultrasound image, thereby generating a 3D color ultrasound image.

Figure 18:
FIG. 18 illustrates a 3D color ultrasound image generated based on the 2D color map according to an exemplary embodiment.
Figure 19:
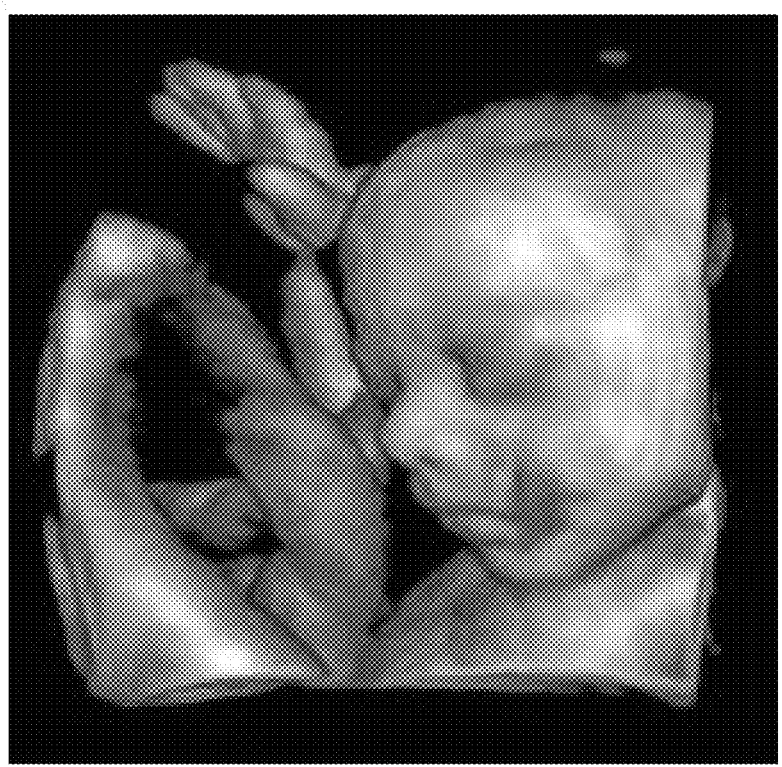
FIG. 19 illustrates a 3D color ultrasound image generated based on a conventional 1D color map.

FIG. 18 is a 3D color ultrasound image generated based on the 2D color map according to an exemplary embodiment. FIG. 19 is a 3D color ultrasound image generated based on a conventional 1D color map. The 3D color ultrasound image of the fetus shown in FIG. 18 is more natural in appearance than that of the 3D color ultrasound image of the fetus shown in FIG. 19, as is readily apparent from comparison therebetween. According to the exemplary embodiments of the present disclosure, the face color and other characteristics of a fetus may be more naturally displayed, and thus, pregnant women and their families may have increased psychological satisfaction and stability.

In addition to the above-described elements of the ultrasonic diagnostic apparatus 1, the ultrasonic diagnostic apparatus 1 may further include a storage unit (not shown). The storage unit may store data or algorithms used to operate the ultrasonic diagnostic apparatus 1. For example, the storage unit may store at least one of an algorithm configured to extract a sample image from baby images, an algorithm configured to convert color space of the sample image, an algorithm configured to perform color gamut modeling on the sample image, an algorithm for generating the 2D color map based on the modeled color gamut, an algorithm for generating volume data based on a plurality of sectional images, an algorithm for performing volume rendering of volume data, and an algorithm needed to generate a 3D color ultrasound image.

The storage unit may be realized as a nonvolatile memory device such as a read only memory (ROM), a programmable read only memory (PROM), an erasable programmable read only memory (EPROM), or a flash memory, a volatile memory device such as a random access memory (RAM), or a storage medium such as a hard disk or an optical disc. However, exemplary embodiments are not limited to the above-described examples, and the storage unit may take other forms known in the art.

Figure 20:
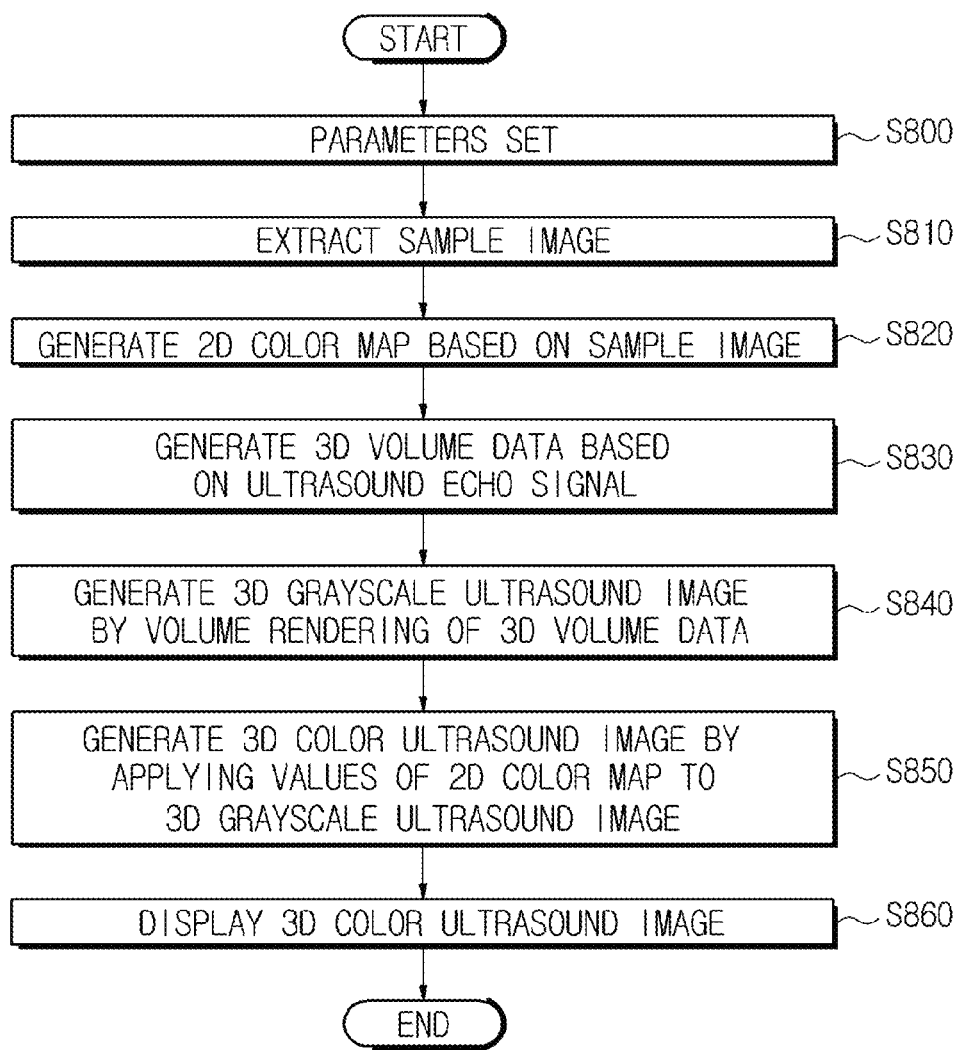
FIG. 20 is a flowchart illustrating a 3D color ultrasound image generation method according to an exemplary embodiment.

FIG. 20 is a flowchart illustrating an ultrasound image generation method according to an exemplary embodiment.

Before starting ultrasonic diagnosis, various parameters used for generation of an ultrasound image are set at operation S800. Examples of the parameters used for generation of an ultrasound image include kinds of baby images, the number of baby images, the number of sample images to be extracted from each baby image, and information as to the shape in which the boundary of the color gamut of the extracted sample image is to be modeled. These parameters may include fixed parameters and adjustable parameters, and operation S800 may be performed only for the adjustable parameters.

When an ultrasonic diagnosis is initiated, the sample image extraction unit 260 extracts a plurality of sample images from a plurality of baby images stored in the database 250 at operation S810. Operation S810 may include determining whether the baby images include faces and surrounding environments, detecting face regions from the baby images according to determination results, and extracting the plurality of sample images from the detected baby face regions.

When the sample images are extracted, the 2D color map generator 270 may generate a 2D color map based on the extracted sample images at operation S820. Operation S820 may include converting a color space of the sample images into YCbCr color space from RGB color space, converting the color space of the sample images into LCH color space from the YCbCr color space, performing polygonal color gamut modeling of the sample images based on color space conversion results, generating the 2D color map by mapping lightness, chroma, and hue corresponding to the polygonal color gamut model to 2D coordinates, and converting lightness, chroma and hue values of each coordinate of the 2D color map into R, G and B values.

When the lightness, chroma, and hue values corresponding to the polygonal color gamut model are mapped to 2D coordinates, the mapping process is performed such that lightness and chroma vary along a horizontal axis of a 2D coordinate system and hue varies along a vertical axis of the 2D coordinate system.

When an ultrasonic diagnosis is initiated, the probe 110 irradiates an ultrasound signal (e.g., to the abdomen of a pregnant woman) and receives an ultrasound echo signal reflected from an object (e.g., fetus inside the abdomen). Thereafter, the control unit 230 generates 3D volume data based on the received ultrasound echo signal at operation S830. Operation S830 may include converting the ultrasound echo signal, which is an analog signal, into a digital signal, receiving and focusing the digital signal to generate plural focused signals, and generating 3D volume data for the object (e.g., fetus) based on the plural focused signals.

Next, the control unit 230 generates a 3D grayscale ultrasound image through volume rendering of the 3D volume data at operation S840. In operation S840, as a volume rendering method, surface rendering or direct volume rendering may be used. In addition, the 3D grayscale ultrasound image generated through volume rendering may be a 2D projection image of the 3D volume data. Each pixel of the 3D grayscale ultrasound image may have a shading value and a depth value.

Once the 3D grayscale ultrasound image has been generated through volume rendering, a 3D color ultrasound image is generated by applying values of the 2D color map to each pixel of the generated 3D grayscale ultrasound image at operation S850. Operation S850 may include searching for shading and depth values of each pixel of the 3D grayscale ultrasound image at horizontal and vertical axes of the 2D color map, respectively, and applying R, G and B values of the searched coordinate to the corresponding pixel of the 3D grayscale ultrasound image.

The generated 3D color ultrasound image is displayed on the main display unit 160 at operation S860. In this regard, the main display unit 160 may be included in the ultrasonic diagnostic apparatus 1, or may be independently installed at a remote location to be in communication with the ultrasonic diagnostic apparatus 1 via wired or wireless communication.

Although the exemplary embodiment of FIG. 20 illustrates that the ultrasound image generation method is performed in a certain order, specifically, in the order of performing operations S830 and S840 after operation S820, the order of the operations may be varied or at least one of the operations may be omitted according to other exemplary embodiments.

For example, the ultrasound image generation method may be performed in a different order from the order shown in FIG. 20, for example, may be performed in the following order of setting of parameters (operation S800), generation of 3D volume data (operation S830), generation of a 3D grayscale ultrasound image (operation S840), extraction of sample images (operation S810), generation of a 2D color map (operation S820), generation of a 3D color ultrasound image (operation S850), and displaying of the 3D color ultrasound image (operation S860).

According to another exemplary embodiment, several operations may be simultaneously performed, for example, operations S810 to S820 may be simultaneously performed and operations S830 to S850 may be simultaneously performed. For this operation, the ultrasonic diagnostic apparatus 1 may include a plurality of control units 230.

According to another exemplary embodiment, if parameters set in operation S800 are the same as those set in previous ultrasonic diagnosis operations, a process (not shown) for reading the 2D color map used in previous ultrasonic diagnosis may be performed, instead of performing operations S810 to S820.

The medical image generating apparatus and medical image generating method according to certain exemplary embodiments have been described above. In addition, other exemplary embodiments may also be implemented through computer readable code/instructions in/on a medium, e.g., a computer readable medium, to control at least one processing element to implement any of the above described exemplary embodiments. The medium may correspond to any medium/media permitting the storage and/or transmission of computer readable code.

The computer readable code may be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as carrier waves. According to the exemplary embodiments, the medium may be a signal, such as a complex signal or bitstream. The media may further include a distributed network, and therefore the computer readable code may be stored, transmitted, and executed in a distributed manner. Moreover, the processing element may include a processor or computer processor, by way of example. The processing element may be distributed and/or included in a single device.

As is apparent from the above description, according to exemplary embodiments, a more realistic color medical image of an object or inner tissues of the object may be generated.

Since a realistic color medical image is provided, user satisfaction for the medical image may be improved.

Although a few exemplary embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. An apparatus configured to generate a medical image, the apparatus comprising:
   a sample image extractor configured to extract aサample image from an original image containing color information of an object;
   a color gamut modeler configured to model a color gamut of the sample image to have a predetermined shape;
   a 2D color map generator configured to generate a 2D color map based on the modeled color gamut;
   a volume data generator configured to generate 3D volume data based on a sectional image of inner tissues of the object; and
   a controller configured to generate a 3D color medical image by applying values of the 2D color map to a 3D grayscale medical image acquired by volume rendering of the 3D volume data.

2. The apparatus according to claim 1, wherein the original image comprises at least one of a captured organ image of a patient, a captured image of blood vessels of a patient, and a baby image obtained by photographing a face of a baby.

3. The apparatus according to claim 2, wherein the sample image extractor extracts the sample image from a face region of the baby image.

4. The apparatus according to claim 3, wherein the apparatus is configured to store, as metadata of the baby image, information indicating whether the baby image comprises both the face region and a surrounding environment or only the face region.

5. The apparatus according to claim 1, wherein the color gamut modeler represents a color gamut of the sample image in a blue-difference chroma component-red-difference chroma component (CbCr) plane of a luma component-blue-difference chroma component-red-difference chroma component (YCbCr) color space and models the color gamut represented in the CbCr plane to have a polygonal shape.

6. The apparatus according to claim 5, wherein the color gamut modeler models the color gamut represented in the CbCr plane into the polygonal shape by representing the color gamut represented in the CbCr plane in a lightness-chroma-hue angle (LCH) color space, dividing a range of hue angles represented in the LCH color space by a number of angles of the polygonal shape, determining points with the highest chroma values respectively corresponding to the divided ranges of the hue angles as vertices of the polygonal shape, and connecting the determined vertices to one another.

7. The apparatus according to claim 5, wherein the color gamut modeler determines values of a hollow region inside the color gamut modeled into the polygonal shape by interpolation.

8. The apparatus according to claim 1, wherein the 2D color map generator generates the 2D color map such that, among lightness values, chroma values and hue values corresponding to the modeled color gamut, the lightness values and the chroma values are mapped along a horizontal axis of 2D coordinates and the hue values are mapped along a vertical axis of the 2D coordinates,
wherein the horizontal axis corresponds to shading values of the 3D grayscale medical image, and
the vertical axis corresponds to depth values of the 3D grayscale medical image.

9. The apparatus according to claim 8, wherein the 2D color map generator converts the lightness values, the chroma values and the hue values of each of a plurality of coordinates of the 2D color map into R, G and B values.

10. The apparatus according to claim 9, wherein the controller generates the 3D color medical image by searching for a coordinate corresponding to the shading values and the depth values of each of a plurality of pixels of the 3D grayscale medical image in the 2D color map and applying R, G and B values of the searched coordinate to each of the corresponding plurality of pixels.

11. A method of generating a medical image, the method comprising:
extracting a sample image from an original image containing color information of an object;
modeling a color gamut of the sample image to have a predetermined shape;
generating a 2D color map based on the modeled color gamut;
generating 3D volume data based on a sectional image of inner tissues of the object; and
generating a 3D color medical image by applying values of the 2D color map to a 3D grayscale medical image acquired through volume rendering of the 3D volume data.

12. The method according to claim 11, wherein the modeling comprises:
representing the color gamut of the sample image in a blue-difference chroma component-red-difference chroma component (CbCr) plane of a luma component-blue-difference chroma component-red-difference chroma component (YCbCr) color space; and
modeling the color gamut represented in the CbCr plane to have a polygonal shape.

13. The method according to claim 11, wherein the generating of the 2D color map comprises generating the 2D color map such that, among lightness values, chroma values and hue values corresponding to the modeled color gamut, the lightness and chroma values are mapped along a horizontal axis of 2D coordinates and the hue values are mapped along a vertical axis of the 2D coordinates,
wherein the horizontal axis corresponds to shading values of the 3D grayscale medical image, and
the vertical axis corresponds to depth values of the 3D grayscale medical image.

14. The method according to claim 13, further comprising converting the lightness values, the chroma values and the hue values of each of a plurality of coordinates of the 2D color map into R, G and B values.

15. The method according to claim 14, wherein the generating of the 3D color medical image comprises:
searching for a coordinate corresponding to the shading values and the depth values of each of a plurality of pixels of the 3D grayscale medical image in the 2D color map; and
applying R, G and B values of the searched coordinate to each of the corresponding plurality of pixels.

16. An apparatus configured to generate a 3D color medical image of an object, the apparatus comprising:
a 2D color map generator configured to generate a 2D color map based on input images extracted from the object;
a volume data generator configured to generate 3D volume data based on the object; and
a controller configured to generate the 3D color medical image based on the 2D color map and the 3D volume data,
wherein the 2D color map generator comprises:
a color gamut modeler configured to model a color gamut of the input images extracted from the object to have a predetermined shape; and
a mapper configured to map values corresponding to the modeled color gamut to 2D coordinates, to thereby generate the 2D color map.

17. The apparatus according to claim 16, wherein the mapper is configured to map lightness values, chroma values, and hue values corresponding to the modeled color gamut to the 2D coordinates, to thereby generate the 2D color map.

18. The apparatus according to claim 17, further comprising a probe configured to transmit an ultrasound signal towards the object and to receive an ultrasound echo signal reflected back from the object,
wherein the volume data generator is configured to generate the 3D volume data based on the reflected ultrasound echo signal.

19. The apparatus according to claim 18, wherein the controller is further configured to perform a volume rendering operation on the 3D volume data to generate a 3D grayscale ultrasound image, and to generate the 3D color medical image based on the 3D grayscale ultrasound image.

20. The apparatus according to claim 19, wherein the volume rendering operation comprises one of a surface rendering operation and a direct volume rendering operation.

* * * * *